United States Patent
Shenoy et al.

(10) Patent No.: US 8,645,152 B1
(45) Date of Patent: Feb. 4, 2014

(54) METHOD FOR PROVIDING MEDICAL TEST RESULTS

(75) Inventors: T. Ashok Shenoy, Macungie, PA (US); Niall Sweeney, Rutherford, NJ (US); Elize Dekker, Ringwood, NJ (US)

(73) Assignee: Quest Diagnostics Investments Inc., Wilmington, DE (US)

( * ) Notice: Subject to any disclaimer, the term of this patent is extended or adjusted under 35 U.S.C. 154(b) by 2256 days.

(21) Appl. No.: 10/044,568

(22) Filed: Jan. 11, 2002

Related U.S. Application Data

(60) Provisional application No. 60/261,315, filed on Jan. 12, 2001.

(51) Int. Cl.
   *G06Q 50/00* (2012.01)
(52) U.S. Cl.
   USPC .................................................. 705/2; 705/3
(58) Field of Classification Search
   USPC .................. 705/2, 3; 600/300, 301; 604/207; 703/11; 707/10, 11
   See application file for complete search history.

(56) References Cited

U.S. PATENT DOCUMENTS

| | | | | |
|---|---|---|---|---|
| 5,737,539 | A * | 4/1998 | Edelson et al. | 705/3 |
| 5,758,095 | A * | 5/1998 | Albaum et al. | 705/2 |
| 6,000,828 | A * | 12/1999 | Leet | 705/2 |
| 6,018,713 | A * | 1/2000 | Coli et al. | 705/2 |
| 6,246,975 | B1 * | 6/2001 | Rivonelli et al. | 703/11 |
| 6,322,502 | B1 * | 11/2001 | Schoenberg et al. | 600/300 |
| 2001/0037217 | A1 * | 11/2001 | Abensour et al. | 705/2 |
| 2002/0010595 | A1 * | 1/2002 | Kapp | 705/2 |
| 2002/0029157 | A1 * | 3/2002 | Marchosky | 705/3 |
| 2002/0035484 | A1 * | 3/2002 | McCormick | 705/2 |
| 2005/0125256 | A1 * | 6/2005 | Schoenberg et al. | 705/2 |

OTHER PUBLICATIONS

Definition for "compensation" on www.dictionary.com.*
Definition for "blood test results" on www.bloodbook.com.*

* cited by examiner

*Primary Examiner* — Dilek B Cobanoglu
(74) *Attorney, Agent, or Firm* — Jon E. Gordon; Frommer Lawrence & Haug LLP

(57) ABSTRACT

In an exemplary embodiment, this invention provides a method of providing medical test results. The method includes a step of selecting formulary information that corresponds to a result of a medical test. The method also includes a step of generating a medical report. The medical report includes a laboratory report that corresponds to the medical test. The medical report also includes the selected formulary information.

9 Claims, 6 Drawing Sheets

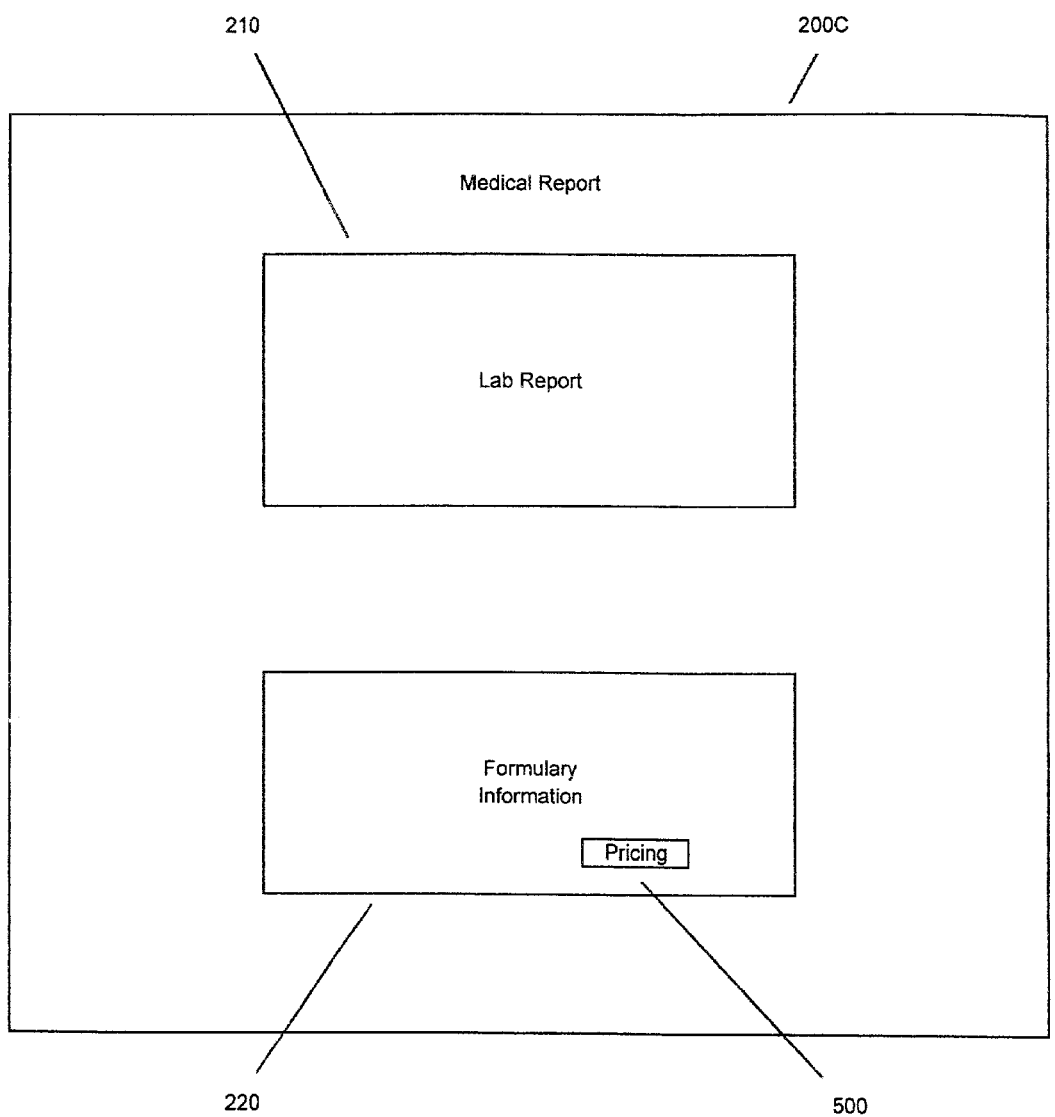

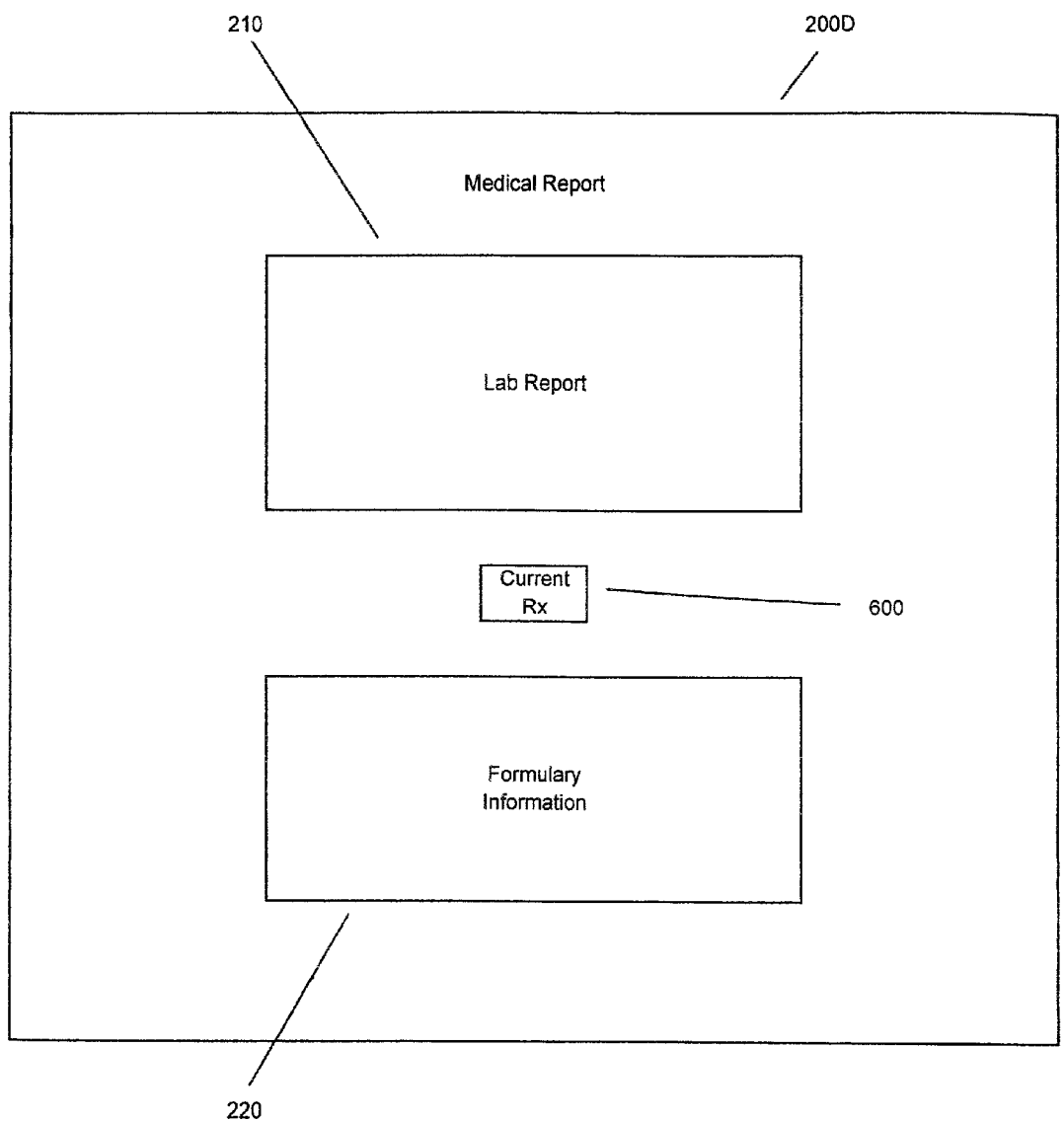

METHOD FOR PROVIDING MEDICAL TEST RESULTS

CROSS-REFERENCE TO RELATED APPLICATION

This application claims the benefit of provisional U.S. Patent Application No. 60/261,315, which was filed on 12 Jan. 2001 and titled "Method for Providing Medical Test Results".

FIELD OF THE INVENTION

This invention relates to a method for providing medical test results. More particularly, this invention relates to a method for providing formulary information relating to medical tests.

BACKGROUND OF THE INVENTION

This invention relates to the healthcare industry, specifically the relationship between physicians (MDs), managed care organizations (MCOs), pharmacy benefit management companies (PBMs), pharmaceutical companies, and patients. MDs treat patients using prescription drugs that are manufactured by pharmaceutical companies. MCOs seek to evaluate and select prescription drugs for particular treatments based upon both healthcare and commercial perspectives, and the MCOs recommend and approve selected prescription drugs for coverage under a managed care contract using what can be referred to as a formulary.

Medical doctors today deal with an average of 5 to 6 MCO (or PBM) plans to which their patients subscribe. When the number of benefits plans is multiplied by the number of possible disease conditions of their patients, the number of formularies that the MDs have to deal with becomes overwhelming. For example, if an MD works with six MCO plans and there are ten disease conditions that they treat, then there may be sixty (60) formularies that they have to remember or be able to refer to prior to selecting a drug for a particular treatment. Accordingly, for each patient that visits a particular MD for treatment for the first time, the MD is likely to identify the patient's MCO and/or PBM plan. Then, for the particular disease state or condition being treated, the MD may have to recollect or research the formulary for the particular MCO and/or PBM before selecting a treatment.

Consequently, medical doctors may prescribe drugs that they remember as being approved, drugs they are most comfortable with, or drugs they consider as standard therapy for the particular disease state. Oftentimes this results in the doctor selecting a drug that is inconsistent with the formulary of the MCO and/or PBM (i.e., the drug that they have prescribed is not the most preferred or, in the worst case, the drug is not even approved by the MCO and/or PBM).

This lack of what is called "formulary compliance" creates many problems in the industry. MCOs and PBMs lose revenue and the patients may also incur an increase in out of pocket expense. The health benefits to the patient may also be reduced. Additionally, the MCOs and PBMs have increased costs in trying to correct the problem immediately at the pharmacy, or in the future with the errant medical doctor through letters and phone calls. The medical doctors also have increased expenses because their staff has to handle the subsequent communications from the providers (MCOs and PBMs) and the pharmacies.

Accordingly, there is a need in the industry for improved formulary compliance.

SUMMARY OF THE INVENTION

In an exemplary embodiment, this invention provides a method of providing medical test results. The method includes a step of selecting formulary information that corresponds to a result of a medical test. The method also includes a step of generating a medical report. The medical report corresponds to the medical test and includes the laboratory report results of the medical test. The medical report also includes the selected formulary information.

In another embodiment, this invention provides a method of providing formulary information that corresponds to the results of a medical test. The method includes a step of identifying a prescription care provider associated with a patient. Further, the method includes the step of selecting formulary information corresponding to a result of the medical test of the patient, and also corresponding to the prescription care provider.

In yet another embodiment, this invention provides a method of treating a patient. The method includes a step of obtaining a medical report including a laboratory report corresponding to a medical test of a patient. The medical report additionally includes formulary information that corresponds to the results of the medical test. The method also includes the step of selecting a treatment for the patient using the formulary information included in the medical report.

In yet another embodiment, this invention provides a medical report for a medical test. The medical report includes a laboratory report corresponding to a medical test of a patient. The medical report also includes formulary information corresponding to the result of the medical test.

In yet another embodiment, this invention provides a method of providing a medical report including formulary information. The formulary information corresponds to one or more selected prescription care providers. The method includes a step of identifying a prescription care provider for a patient. The method also includes the step of verifying that the prescription care provider for the patient is one of the selected prescription care providers. Further, the method also includes the step of generating a medical report including the formulary information corresponding to the prescription care provider for the patient.

BRIEF DESCRIPTION OF THE DRAWINGS

The invention will be described with reference to the exemplary embodiments illustrated in the figures of which:

FIG. 5 is an illustration of still another embodiment of a medical report in accordance with aspects of the present invention.

FIG. 6 is an illustration of another embodiment of a medical report in accordance with aspects of the present invention.

DETAILED DESCRIPTION OF THE INVENTION

Figure 1:
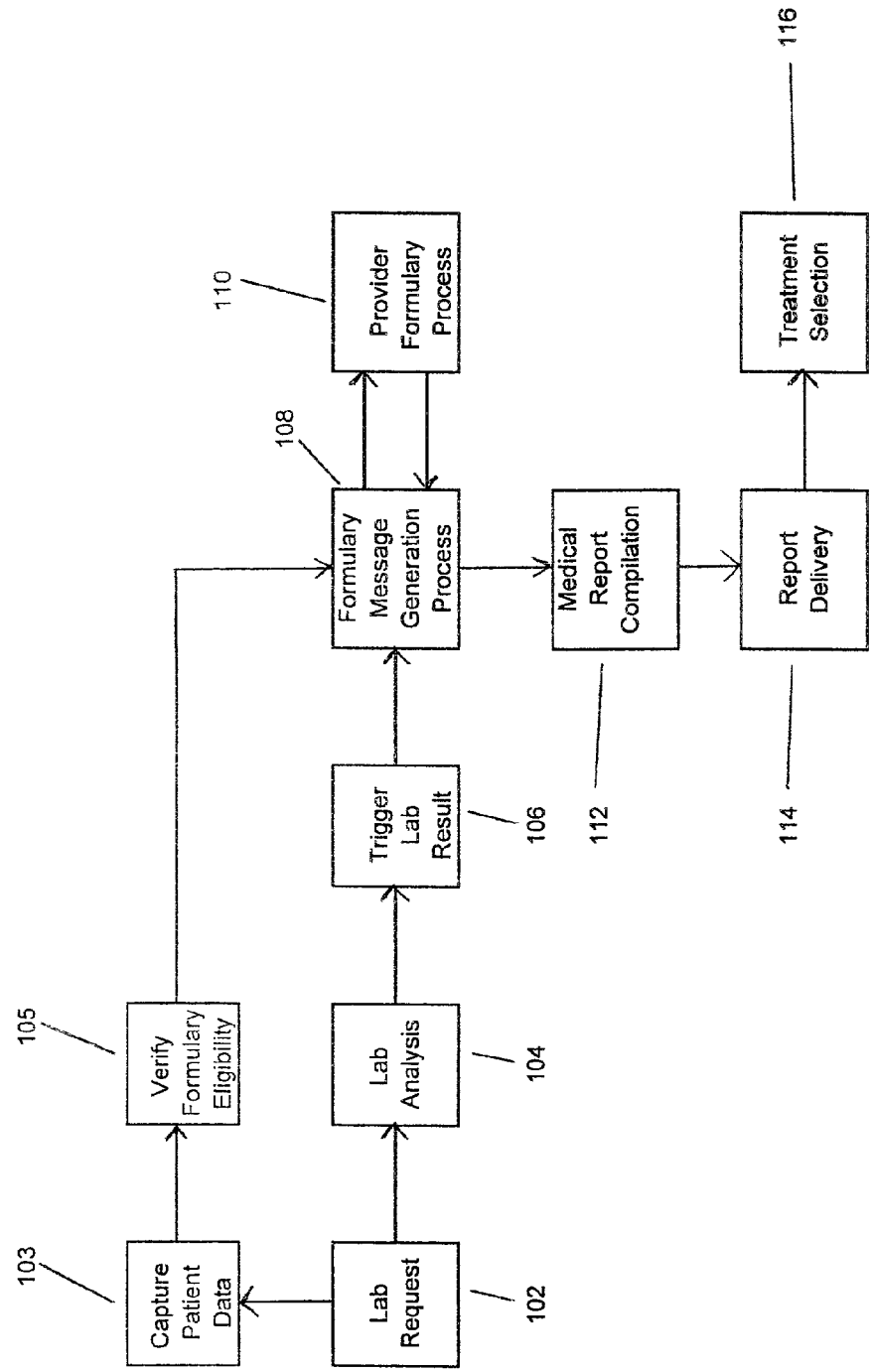
FIG. 1 is a flow diagram which illustrates an exemplary embodiment of a method of delivering a medical report in accordance with aspects of the present invention.

Preferred features of selected, exemplary embodiments of this invention will now be described with reference to the figures. It will be appreciated that the spirit and scope of the invention is not limited to the embodiments selected for illustration. It is contemplated that any of the configurations described hereafter can be modified within the scope of the invention.

In one exemplary embodiment, the medical test results are laboratory test results. Throughout this document the term medical test results is intended to identify a broad class of test results, which includes laboratory test results as well as any other results relating to a medical evaluation. For example, a medical test result could be a laboratory test result, such as the result obtained for a blood specimen or other type of biological specimen is examined. Alternatively, a medical test result may be a blood pressure test result, a stress test result, a cardiogram, or a result of any medical evaluation.

Generally, with reference to FIGS. 1 through 6, one aspect of this invention provides a method of providing medical test results. Formulary information 220 corresponding to a result of a medical test is selected at a formulary message generation process step 108. The formulary information is optionally provided in the form of formularies, which can be formatted as lists of approved drugs for a certain disease or condition. Each formulary list can be broken down by those approved drugs that are preferred ("tier 1"), less preferred ("tier 2") and non-preferred ("tier 3"). These formularies are usually disease state and MCO plan specific. A medical report 200 is generated at a medical report compilation step 112. The medical report includes a laboratory report 210 corresponding to the medical test. The medical report also includes the selected formulary information 220.

In another aspect this invention provides a method for providing formulary information 220 corresponding to results of a medical test. This method includes confirming that a patient is associated with either a health care insurer or prescription benefit management company for their prescription benefits (i.e., a prescription care provider) and qualifies for the formulary to be listed. Further, formulary information 220 corresponding to a result of a medical test of the patient, and also corresponding to the prescription care provider, is selected at a formulary message generation process step 108. Additionally, the formulary information 220 is provided to a medical professional in a report delivery step 114.

In another aspect, this invention provides a method of treating a patient. This method includes the step of obtaining a medical report 200 at report delivery step 114. The medical report 200 includes a laboratory report 210 that corresponds to a medical test of a patient. The medical report 200 also includes formulary information 220 that corresponds to a result of the medical test. The method also includes the step of selecting the treatment for the patient at step 116 using the formulary information 220 in the medical report 200.

In yet another aspect, this invention provides a medical report 200 for a medical test. The medical report 200 comprises a laboratory report 210 that includes a result of a medical test of the patient. The medical report 200 also includes formulary information 220 that corresponds to the result of the medical test.

In yet another aspect, this invention provides a method of providing a medical report 200 including formulary information 220. The formulary information 220 corresponds to one or more selected prescription care providers. A prescription care provider for a patient is identified and captured at a capture patient data step 103. At step 105 it is verified that the prescription care provider for the patient is one of the selected prescription care providers. A medical report including the formulary information corresponding to the prescription care provider for the patient is generated at steps 108 and 112.

"Formulary information" as used herein refers to any information, sometimes in the form of one or more lists, regarding an approved drug or drugs for a certain disease or condition or indication. The formulary information is usually provider specific. In an exemplary embodiment, the provider may be a managed care organization (MCO). In another exemplary embodiment, the provider may be a pharmacy benefit management company (PBM). According to one embodiment, the formulary list separates the approved drugs into numerous tiers, such as tier 1, tier 2 and tier 3. Tier 1 drugs are those that are most preferred by the provider, tier 2 drugs are less preferred by the provider, and tier 3 drugs are non-preferred by the provider. A medical professional (e.g., a doctor) can use the formulary information in order to make a prescription or treatment decision related to a patient.

When a patient undergoes a medical procedure or test or other evaluation that involves a laboratory analysis, a clinical laboratory report is typically generated. The clinical laboratory report, hereafter referred to as the laboratory report or the lab report, includes all of the results of the medical test performed. This means that the laboratory report not only includes abnormal medical test results (i.e., results outside a "normal" range), but also includes normal medical test results (i.e., results within a "normal" range).

If abnormal medical test results are reported separately from normal medical test results (i.e., in a partial, preliminary report as opposed to a complete laboratory report), formulary information can be provided at a later time together with a supplemental, second report that includes the normal medical test results. Alternatively, it may be preferred to make the formulary information available with the complete laboratory report at the time that the laboratory report is first issued. By providing the formulary information together with the laboratory report (e.g., in a first report from a laboratory testing company to the medical professional as opposed to in a second report), the formulary information will be made available to the medical professional at the time when he or she makes a treatment or prescription decision. In other words, by providing the formulary information together with the complete laboratory report in a first (and perhaps only) medical report from the laboratory testing company, the medical professional can utilize the formulary information at the same time he or she evaluates the laboratory report and makes a treatment decision.

It has been discovered that the provision of the formulary information together with the complete laboratory report is beneficial because it avoids the need for a second report. Such a second report may be received by the medical professional after a treatment decision has already been made, based on a first report of abnormal test results, without the benefit of having the formulary information. Also, the use of a second report may add to the administrative burden of the medical professional because it must be reported to the patient, filed with the patient's medical history, or otherwise handled or considered by the medical professional.

Therefore, it has been discovered that it may be preferred to include the formulary information along with the complete laboratory report in a medical report that is delivered to the medical professional. That medical report, according to an exemplary embodiment of this invention, is the first and only report sent to the medical professional by the laboratory testing company.

It is therefore understood that a single medical report (including a clinical laboratory report) may be generated and delivered to a medical professional with appropriate formulary information. Alternatively, multiple medical reports may be generated and delivered, with each of the reports including the appropriate formulary information. In another aspect, multiple medical reports may be generated and delivered, with the first (original) report including the appropriate formulary information. In each of these exemplary aspects, the medical professional may have a medical report (including the formulary information) before making a treatment decision (e.g., a prescription). Therefore, the medical professional can have the benefit of the formulary information at the time that a treatment decision is made.

According to one exemplary embodiment, the medical report 200 includes a laboratory report 210 and formulary information 220. The laboratory report 210 is the first results that a medical professional receives related to the medical test performed. Therefore, because the formulary information 220 is included in the medical report 200 along with the laboratory report 210, the medical professional receives the formulary information 220 at the earliest possible opportunity. Therefore, the medical professional can utilize the formulary information 220 in order to make an appropriate treatment or prescription decision. As a result, formulary compliance is increased.

FIG. 1 illustrates an exemplary embodiment of a method of providing medical test results to a medical professional. A lab request 102 is typically made by a physician or other medical professional regarding a condition or potential condition of a patient. Lab request 102 is sent to one of a number of laboratories that may belong to a lab information systems network. The laboratory that receives lab request 102 performs the lab analysis at a step 104. The results of lab analysis step 104 may include abnormal medical test results, along with normal medical test results. Alternatively, the results of lab analysis step 104 may be entirely normal or entirely abnormal.

At least one element of the results of lab analysis step 104 results in a trigger 106. Trigger 106 may be an abnormal test result from lab analysis 104, or trigger 106 may be a normal test result from lab analysis 104. Regardless of the test result that caused trigger 106, trigger 106 results in the initialization of a formulary message generation process step 108.

In parallel to the steps described above, lab request 102 additionally initializes a data capture step 103. At step 103 patient data is captured in preparation for the potential compilation of a medical report. For example, the patient data captured may include patient identification information, patient insurance information (e.g., a policy number), and other relevant information that can be retrieved in advance of (or concurrently with) the lab analysis being conducted. The patient insurance information captured preferably includes the identity of the patient's prescription care provider (e.g., MCO, PBM).

After the patient data is captured at step 103, the eligibility of a formulary message is verified at step 105. For example, certain providers may subscribe to a formulary messaging service according to exemplary embodiments of this invention. As such, medical reports issued relating to patients associated with these subscribing providers may be selected to include relevant formulary information. Inclusion of relevant formulary information may further be conditioned upon the specific policy (or type of policy) that the patient has with the provider.

Other providers may not subscribe to the formulary messaging service. As such, medical reports issued relating to patients associated with these non-subscribing providers may not include relevant formulary information. Therefore, at step 105, the eligibility of a formulary message to be included in a medical report is verified.

For example, one or more benefits providers (such as a medical insurance company) may subscribe to a formulary messaging service that is provided by a reporting entity that generates medical reports (such as a laboratory testing company). As a subscriber, the benefits provider makes formulary guidelines available to the reporting entity. When a test is performed for patient that subscribes to the benefits provider and a medical report is to be generated for that patient, the formulary guidelines of the subscribing benefits provider are incorporated into the medical report. In that way, formulary guidelines of subscribing benefits providers are made available to the medical professional acting on behalf of the patient.

After the eligibility of the inclusion of formulary information is verified at step 105, the data captured at step 103 is transmitted to the formulary message generation process step 108.

The formulary message generation process step 108 may be conducted by the laboratory that received lab request 102, for example, by utilizing a computer server internal to the laboratory. Alternatively, formulary message generation process step 108 may be conducted by a central server that compiles formulary message generation processes 108 for a number of laboratories. In order to to conduct the formulary message generation process step 108, formulary information specific to the trigger 106 (e.g., a disease state, an abnormal test result, a normal test result, etc.), and formulary information specific to a provider (e.g., an insurance provider) of the patient may be utilized.

The insurance provider of the patient may be a medical insurance provider, such as a managed care organization (MCO). Alternatively, the provider of the patient may be a pharmacy benefit management company (PBM). In some situations, the MCO of the patient and the PBM of the patient may be the same company.

The server utilized to conduct formulary message generation process step 108 requests information from the provider at provider formulary process step 110. For example, according to one exemplary embodiment, the requested information will include an indication of whether the MCO of the patient and the PBM of the patient are the same company. The requested information may also include eligibility information, co-pay information, pricing information, or additional medical or treatment guidelines. However, the primary request at step 110 is for the relevant formulary information.

If the MCO is also the prescription care provider for the patient, the formulary information provided by the provider formulary process step 110 to the formulary message generation process step 108 will be MCO specific. However, if the MCO is not the prescription care provider of the patient, and indeed a distinct PBM is the prescription care provider of the patient, the formulary information provided by provider formulary process step 110 to formulary message generation process step 108 will be PBM specific.

The storage and/or provision of formulary information, in to provider formulary process step 110, can be performed by a prescription drug provider such as an MCO or a PBM, by a third party managing the process on behalf of the prescription drug provider, or by some other entity capable of manipulating or otherwise handling formulary information.

Upon receiving the requested information from provider formulary process step 110, formulary message generation process step 108 will provide the appropriate formulary message to the laboratory (or whichever entity compiles the medical report) so that the medical report may be compiled in a medical report compilation step 112. At medical report compilation step 112, a medical report 200 is generated that includes the lab report 210 and the formulary message (formulary information) 220. Because the formulary information 220 is available at the same time that the laboratory report is available, a timely medical report 200 may be compiled. The medical report is then delivered to the appropriate medical professional at report delivery step 114.

The medical report 200 may be delivered to a physician, or any other appropriate medical professional. The medical report 200 may be delivered by any appropriate means such as courier, mail, printer e-mail, fax, or other electronic or wireless devices such as a personal digital assistant (PDA). In an exemplary embodiment, the medical report 200 is delivered by the same means by which the laboratory test was ordered by the medical professional. For example, if the laboratory test was ordered electronically, then the medical report is advantageously delivered electronically to the same address from which the test was ordered. Alternatively, if the laboratory test was ordered via hard copy requisition, picked up by a laboratory courier, then the medical report is advantageously delivered to the same address by a laboratory courier.

Upon reviewing the medical report 200, the medical professional will have access to accurate formulary information that is specific to the medical test result, insurance provider, and the patient. The medical professional may then select appropriate treatment for the patient at treatment selection step 116. As a result of this process, treatment (e.g., a prescription) is selected for the patient that is in compliance with the formulary.

In the event that the medical report is delivered electronically via the Internet, the medical professional may be provided with the option to access available online prescribing systems 118 directly from the medical report using hyperlinks. For example, if the medical report is provided by electronic mail, a link such as a hyperlink can be provided within the medical report for immediate electronic access to one or more electronic prescription services. In that way, the medical professional can easily prescribe a particular drug or other treatment based on the test results and formulary information found in the medical report.

Figure 2:
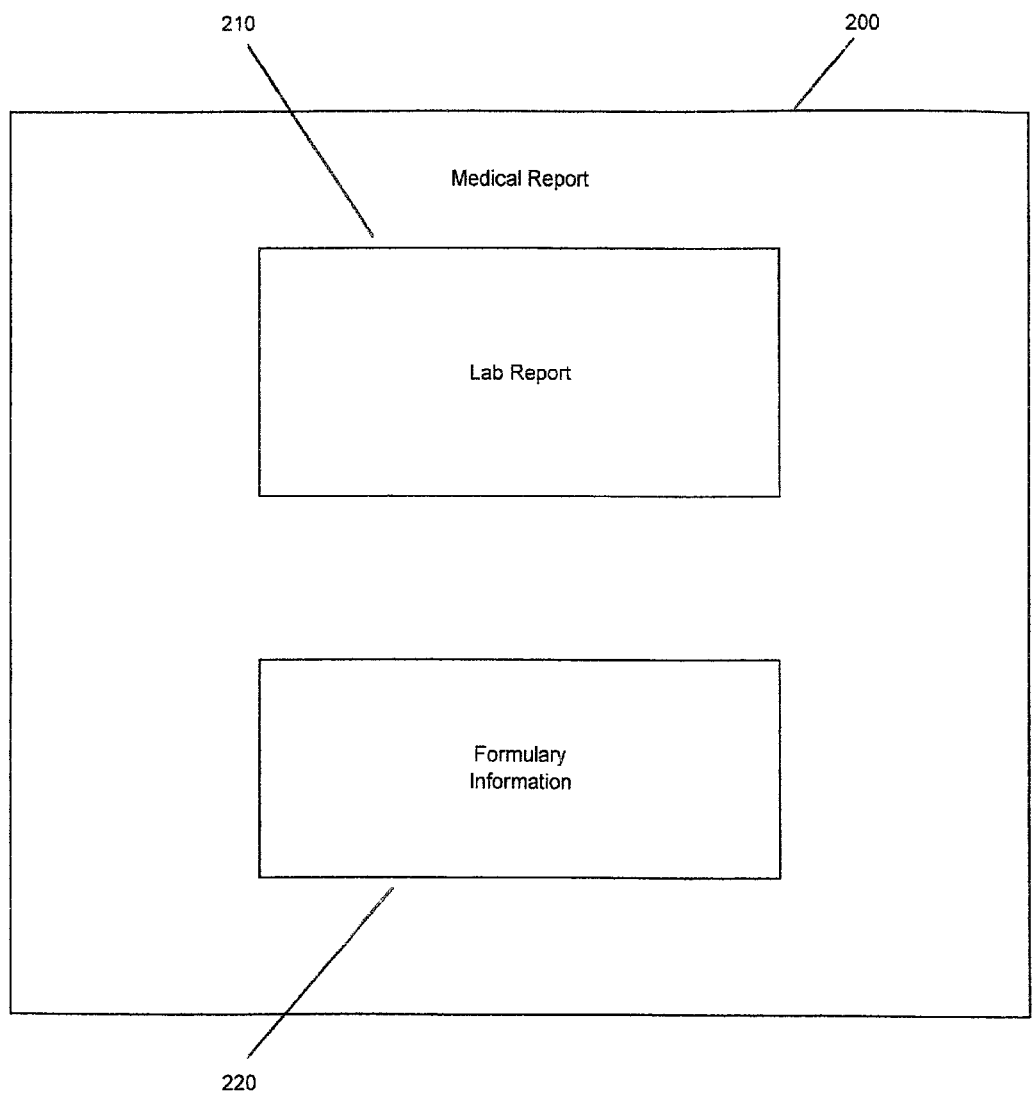
FIG. 2 is an illustration of an embodiment of a medical report in accordance with aspects of the present invention.

FIG. 2 illustrates a medical report 200 in accordance with an exemplary embodiment of the present invention. The medical report 200 includes a lab report 210. The medical report 200 also includes formulary information 220. The lab report 210 included in the medical report 200 is the complete laboratory report. The lab report 210 includes any normal medical test results produced by the test along with any abnormal medical test results. The lab report 210 is the initial or first or only medical test result that a medical professional will receive relating to the requested medical test. Therefore, since the formulary information 220 is included in the medical report 200 along with the initial lab report 210, the medical professional reviewing the medical report 200 can make a compliant treatment decision based on the relevant formulary information.

The medical report 200 may include any other relevant or helpful information. For example, the medical report 200 may optionally include patient specific information. The patient specific information may include the patient's name, the patient's date of birth, any allergies the patient may have, and any other relevant information regarding the patient. The medical report 200 may also include the date that the respective medical test was performed. For example, if a laboratory specimen was taken from a patient and sent to a lab to be tested, the date that the specimen was taken may be included in the medical report 200. In addition to the date of the specimen or laboratory test, the time of the laboratory test may also be included in the medical report 200. As such, any relevant information may be included in medical report 200, and such relevant information can be selected depending on the preferences of the medical professional, the laboratory testing company, and/or some other entity.

Figure 3:
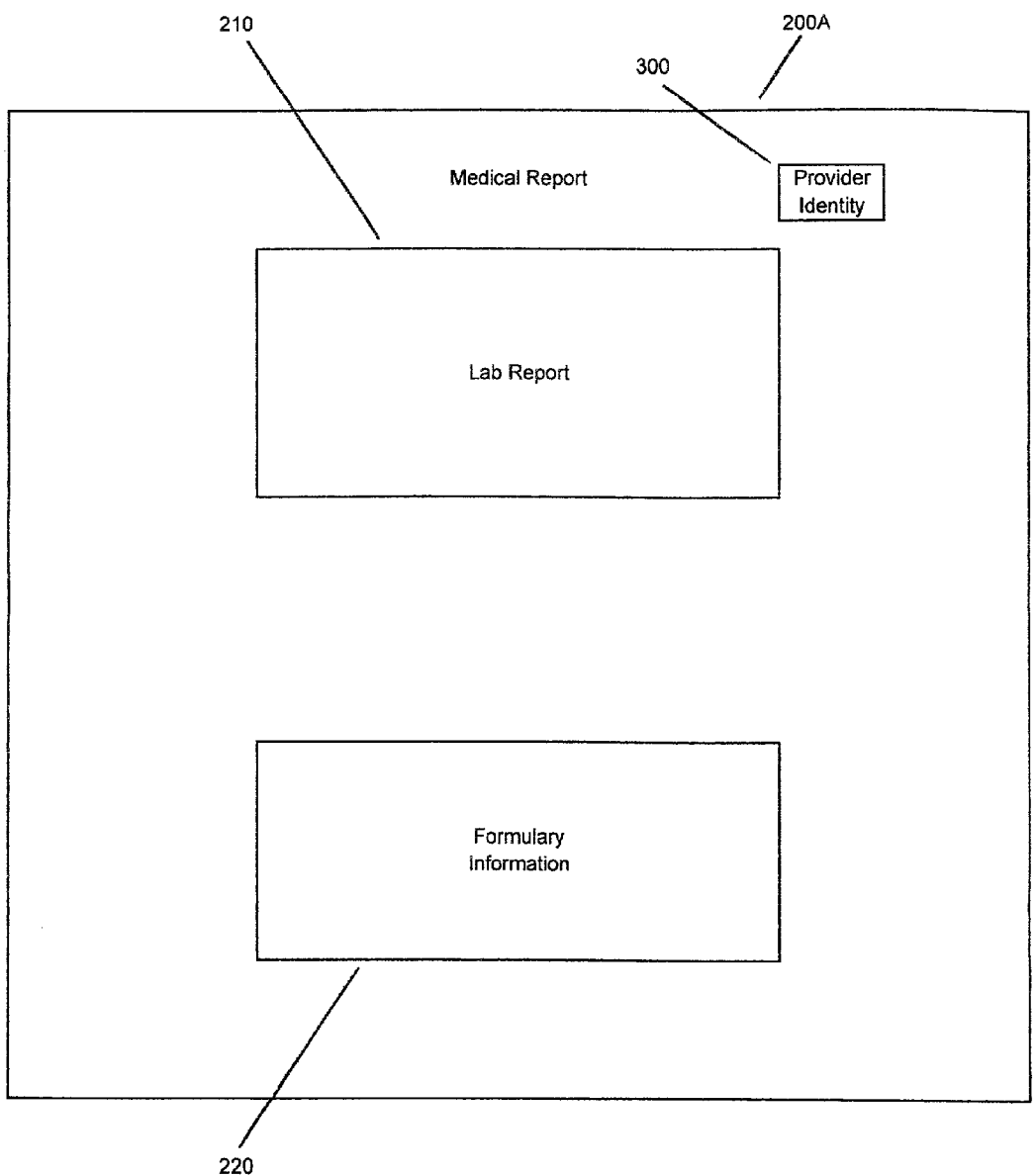
FIG. 3 is an illustration of another embodiment of a medical report in accordance with aspects of the present invention.

FIG. 3 illustrates a medical report 200A in accordance with another exemplary embodiment of the present invention. The medical report 200A includes the lab report 210 and the formulary information 220, as in FIG. 2. However, the medical report 200A illustrated in FIG. 3 additionally includes a provider identity 300. If the patient's MCO is the same as the patient's prescription care provider, then the provider identity would be the identity of the MCO. However, if the patient's MCO is different from the patient's prescription care provider (e.g., PBM), then the provider identity 300 would be the identity of the prescription care provider of the patient. The provider identity 300 may be useful to the medical professional in making a treatment decision, and it may therefore be preferred that the provider identity 300 is included in the medical report 200A.

Although the identity of the provider 300 is shown in an area of the medical report 200A that is different from the lab report 210 or the formulary information 220, this is not required. Therefore, the identity of the provider 300 may be included in the formulary information section 220 of the medical report 200A, or it may be included in the lab report 210 section of the medical report 200A or elsewhere depending upon preferences of the entity creating the report.

Figure 4:
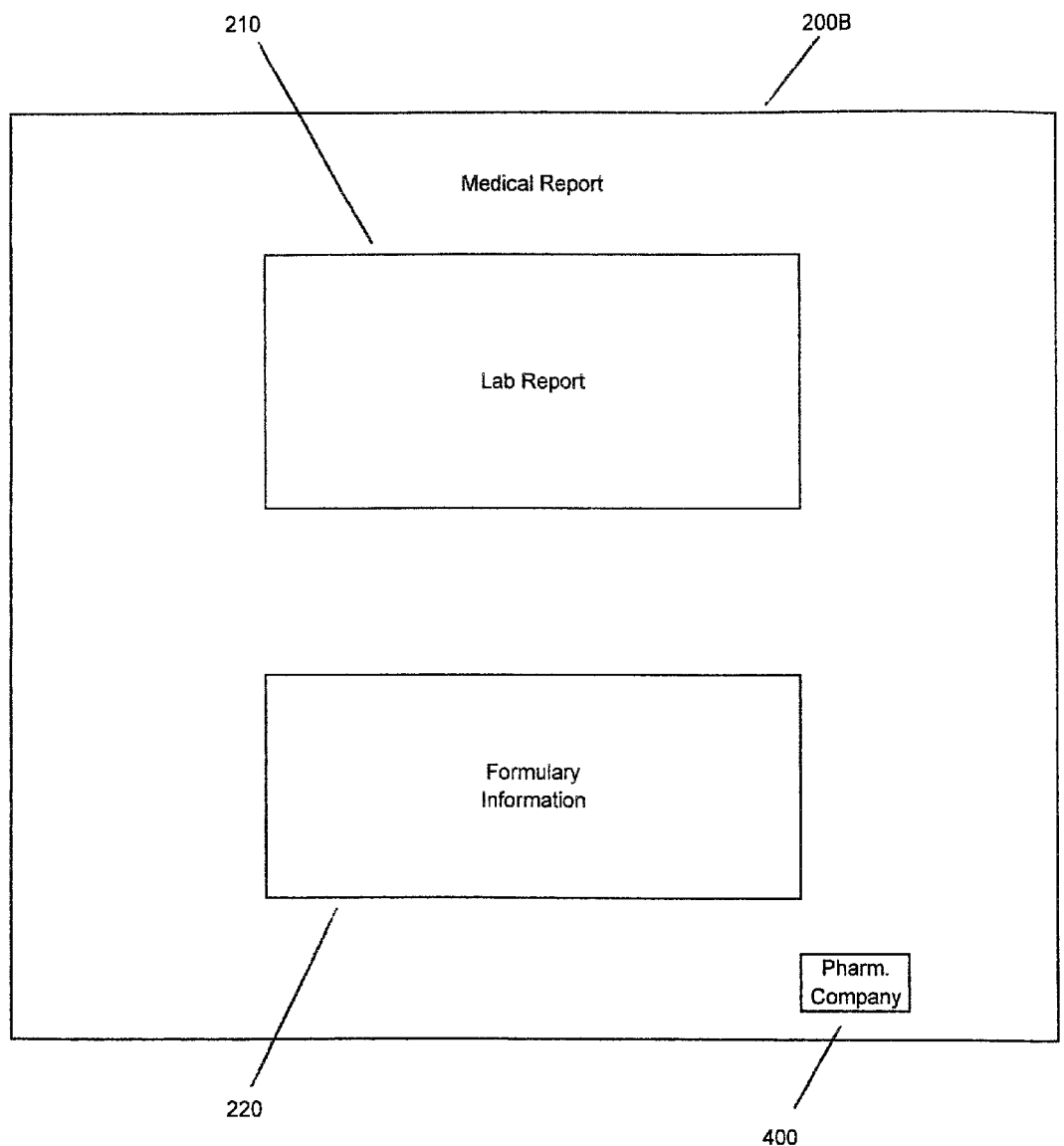
FIG. 4 is an illustration of yet another embodiment of a medical report in accordance with aspects of the present invention.

FIG. 4 illustrates another medical report 200B in accordance with an exemplary embodiment of the present invention. As with the previously described embodiments, the medical report 200B illustrated in FIG. 4 includes the lab report 210 and the formulary information 220. However, the medical report 200B illustrated in FIG. 4 additionally includes the pharmaceutical company identity 400 or the identity of another supplier. For example, a pharmaceutical company may be a manufacturer of a drug or treatment option included in the formulary information 220.

The pharmaceutical company 400 may be a subscriber to a formulary messaging service provided by the lab (or whichever entity generates the medical report). As a subscriber, the pharmaceutical company 400 may desire to have its logo included in the medical report 200B. Additionally, during preparation of the medical report 200B, the laboratory (or an alternative medical report compiler) may provide a subscribing pharmaceutical company 400 with additional benefits with regard to the medical report 200B. For example, if the pharmaceutical company 400 has a tier 1 preferred drug included in the formulary list in formulary information 220, the pharmaceutical company listing may be distinguished from other pharmaceutical companies listings in the formulary listing. For example, the pharmaceutical company listing may be enlarged with respect to the other pharmaceutical companies listings, or the pharmaceutical company listings may be included in a bold typeface. By distinguishing the pharmaceutical company listing, the pharmaceutical company hopes that the medical professional reviewing the medical report may be inclined to select the pharmaceutical company's drug or treatment option.

Although the identity of the pharmaceutical company 400 is shown in area of the medical report 200B that is different from the lab report 210 or the formulary information 220, this is not required. Therefore, the identity of the pharmaceutical company 400 may be included in the formulary information section 220 of the medical report 200B, or it may be included in the lab report 210 section of the medical report 200B or elsewhere.

FIG. 5 provides an additional illustration of a medical report 200C in accordance with another exemplary embodiment of the present invention. As with the previously described embodiments, the medical report 200C illustrated in FIG. 5 includes lab report 210 and formulary information 220. However, the medical report 200C illustrated in FIG. 5 includes optional pricing information 500. Pricing information 500 may represent the price of each treatment option on the formulary listing in formulary information 220. Pricing information 500 may be an average wholesale price of each treatment option. Alternatively, pricing information 500 may represent an average retail price of each treatment option. Pricing information 500 will assist the medical professional in selecting a cost-effective, yet compliant treatment option from formulary information 220.

FIG. 6 illustrates yet another medical report 200D in accordance with still another exemplary embodiment of the present invention. As with the previously described embodiments, medical report 200D includes lab report 210 and formulary information 220. However, medical report 200D illustrated in FIG. 6 includes optional current prescriptions information 600. The patient's current prescription information may assist the medical professional in selecting a treatment option from the formulary information listing 220. For example, the patient's current prescription information may reveal that a certain drug included in the formulary information listing 220 may not be utilized by the patient. Conversely, the patient's current prescription information 600 may make a treatment option included in the formulary information listing 220 more desirable than the alternative treatment included in formulary listing.

Although the patient's current prescription information 600 is illustrated in an area of the medical report 200D that is distinct from the lab report 210 and the formulary information 220, this is not required. Therefore, the patient's current prescription information 600 may be included in the formulary information section 220, or may be included in the lab report section 210 or elsewhere.

As indicated above, medical report 200 may optionally include additional information not shown in any of the figures of the present application. For example, medical report 200 may include additional medical guidelines or medical interactions. The medical guidelines or medical interactions may be specific to the trigger medical test result 106. For example, if the trigger 106 medical test result was an abnormal hemoglobin test result, than the medical guidelines or medical interactions included in medical report 200 may include medical guidelines related to abnormal hemoglobin results. The guidelines may include treatment, dietary, technical, or any other information relevant to the hemoglobin result trigger 106.

As provided above, medical report 200 is delivered to a medical professional at report delivery step 114. The medical report 200 may be delivered to the medical professional through any of a number of communication means. For example, medical report 200 may be printed and couriered to the medical professional. Alternatively, medical report 200 may be printed and mailed to the medical professional, may be faxed to the medical professional, may be e-mailed or otherwise electronically transmitted to the medical professional, or may be delivered to the medical professional using any other electronic method such as by the use of a personal digital assistant (PDA). Because the medical report 200 may be delivered electronically to the medical professional, the medical report 200 may exist in electronic form only.

The medical report disclosed herein may typically be used in making treatment decisions by a medical professional. The medical report may include information, such as a web address, that may be used by the medical professional to prescribe the treatment online. In addition to this information, the medical report may include instructions to assist the medical professional in prescribing the treatment online. Further, if the medical report is provided electronically, the report may include a link to an online prescription service.

It will be appreciated that other modifications can be made to the illustrated embodiments without departing from the scope of the invention. The scope of the invention separately defined in the appended claims.

We claim:

1. A computer system for providing a result of a laboratory test performed upon a patient who participates in a prescription drug benefit plan that is associated with a prescription care provider, the system comprising:
   one or more programmable processors; and
   a non-transitory computer-readable storage medium, operatively coupled to one or more of the processors, the medium being encoded with instructions that, when executed by one or more of the processors, cause the computer system at least to select formulary information, associated with the result of the laboratory test, from a prescription drug formulary that is associated with the provider and is applicable to the patient, the formulary information comprising information about the provider's coverage of one or more prescription drugs;
   wherein the computer-readable storage medium is encoded with instructions that cause the computer system at least to select, based on the test result, one or more treatment options; and
   the selected formulary information, comprised by the medical report, comprises information identifying the selected one or more treatment options;
   and wherein the computer-readable storage medium is encoded with instructions that cause the computer system
   to identify a sponsor of the medical report and
   to cause the medical report to comprise information that distinguishes a treatment option, identified in the formulary information, that is associated with the sponsor from one or more alternative treatment options identified in the formulary information
   and generate a medical report that comprises the result of the laboratory test and the selected formulary information.

2. The computer system of claim 1, wherein:
   The computer-readable storage medium is encoded with instructions that, when executed by one or more of the processors, cause the medical report to identify one or more current prescriptions of the patient.

3. The computer system of claim 1, wherein the computer-readable storage medium is encoded with instructions that cause the computer system at least to identify the prescription care provider associated with the patient.

4. The computer system of claim 3, wherein:
   the prescription care provider associated with the patient is a pharmacy benefit management company;
   the patient is associated with a medical insurance provider other than the pharmacy benefit management company; and
   the computer-readable storage medium is encoded with instructions that cause the computer system to select the insurance provider of the patient that is the prescription care provider.

5. A method, using a computer system that comprises at least one programmable processor and a non-transitory computer-readable storage medium that is operatively coupled to the processor and encoded with instructions that the processor is capable of executing, of providing a result of a medical test performed upon a patient who participates in a prescription drug benefit plan that is associated with a prescription drug benefit plan that is associated with a prescription care provider, the method comprising:

receiving the result of the laboratory test through at least one interface that is operatively coupled to at least one of the processors;

at least one of the processors executing instructions retrieved from the computer-readable storage medium to cause selection of formulary information, associated with the result of the laboratory test, from a prescription drug formulary that is associated with the provider and is applicable to the patient, the formulary information comprising information about the provider's coverage of one or more prescription drugs, at least one of the processors executing instructions retrieved from the computer-readable storage medium to cause selection, based on the test result, of one or more treatment options, wherein generation of the medical report comprises including in the medical report information identifying the selected one or more treatment options, at least one of the processors executing instructions retrieved from the computer-readable storage medium to cause identification of a sponsor of the medical report, wherein generation of the medical report comprises including in the medical report information that distinguishes a treatment option, identified in the formulary information, that is associated with the sponsor from one or more alternative treatment options identified in the formulary information, generation of a medical report that comprises the result of the laboratory test the comprises the result of the laboratory test and the selected formulary information; and transmitting the report through at least one interface that is operatively coupled to at least one of the processors.

6. The method of claim 5, comprising at least one of the processors executing instructions retrieved from the computer-readable storage medium to cause identification of one or more current prescriptions of the patient, wherein generation of the medical report comprises including in the medical report information identifying one or more of the identified current prescriptions.

7. The method of claim 5, comprising at least one of the processors executing instructions retrieved from the computer-readable storage medium to cause identification of the prescription care provider that is associated with the patient.

8. The method of claim 7, wherein the prescription care provider that is associated with the patient is a pharmacy benefit management company, the method comprising:

receiving through at least one interface that is operatively coupled to at least one of the processors information indicating that the patient is associated with a medical insurance provider other than the pharmacy benefit management company; and at least one of the processors executing instructions retrieved from the computer-readable storage medium to cause selection of the insurance provider of the patient that is the prescription care provider.

9. The method of claim 5, wherein:

transmitting the medical report comprises transmitting the medical report to a means for delivering the medical report to a medical professional who ordered the medical test for the patient; and the transmitting of the medical report is the first transmission of the result of the medical test to a means for delivering the medical report to the medical professional who ordered the medical test for the patient.

* * * * *